US00PP32103P2

(12) United States Plant Patent
Nishikawa

(10) Patent No.: US PP32,103 P2
(45) Date of Patent: Aug. 18, 2020

(54) ***DELOSPERMA* PLANT NAMED 'WOW312'**

(50) Latin Name: *Delosperma nubigenum*
Varietal Denomination: Wow312

(71) Applicant: Koichiro Nishikawa, Okayama (JP)

(72) Inventor: Koichiro Nishikawa, Okayama (JP)

( * ) Notice: Subject to any disclaimer, the term of this patent is extended or adjusted under 35 U.S.C. 154(b) by 0 days.

(21) Appl. No.: 16/501,800

(22) Filed: Jun. 7, 2019

(30) Foreign Application Priority Data

Apr. 4, 2019 (QZ) ..... PBR 2019/0863

(51) Int. Cl.
*A01H 5/02* (2018.01)
*A01H 6/30* (2018.01)

(52) U.S. Cl.
USPC ..... Plt./422

(58) Field of Classification Search
USPC ..... Plt./422
See application file for complete search history.

*Primary Examiner* — Susan McCormick Ewoldt
(74) *Attorney, Agent, or Firm* — Penny J. Aguirre

(57) ABSTRACT

A new cultivar of *Delosperma* plant named 'Wow312' that is characterized by its low-growing plant habit, its long blooming period and its flowers that have bright white petal tips, white center eye and bright yellow in the mid-section.

2 Drawing Sheets

Botanical classification: *Delosperma nubigenum.*
Variety denomination: 'Wow312'.

CROSS REFERENCE TO RELATED APPLICATIONS

This application is related to U.S. Plant Patents derived from the same breeding program that are entitled *Delosperma* Plant Named 'WOW2011-1' (U.S. Plant Pat. No. 25,684) and *Delosperma* Plant Named 'Jewel of Desert Peridot' (U.S. Plant Pat. No. 23,566). This application claims priority to European Community Plant Variety Office (CPVO) Plant Breeder's Rights Application No. 2019/0863 filed on Apr. 4, 2019, the entire contents of which is incorporated by reference herein.

BACKGROUND OF THE INVENTION

The present invention relates to a new and distinct cultivar of *Delosperma* plant, botanically known as *Delosperma nubigenum* 'Wow312' and will be referred to hereinafter by its cultivar name, 'Wow312'. The new cultivar of *Delosperma* is an herbaceous perennial grown for container and landscape use.

The new cultivar in Ichinimiya-City, Aichi-Pref, Japan. The overall purpose of the breeding program was to develop new cultivars of *Delosperma* plants with low-growing and well-spreading growth habits combined with long flowering periods and a unique range of flower colors.

'Wow312' arose from crosses made by the Inventor between unnamed and unpatented proprietary plants of *Delosperma nubigenum* from his breeding program. Seeds were pooled from the crosses and therefore the exact parentage is unknown. 'Wow312' was selected in May of 2013 as a single unique plant amongst the resulting seedlings.

Asexual propagation of the new cultivar was first accomplished by stem cuttings in September of 2013 by the Inventor in Ichinimiya-City, Aichi-Pref, Japan. Propagation by stem cuttings has shown that the unique features of the new cultivar are stable and reproduced true to type in successive generations.

SUMMARY OF THE INVENTION

The following traits have been repeatedly observed and are determined to be the characteristics of the new cultivar. These attributes in combination distinguish 'Wow312' as a unique cultivar of *Delosperma.*

1. 'Wow312' exhibits a low-growing plant habit.
2. 'Wow312' exhibits a long blooming period.
3. 'Wow312' exhibits flowers that have bright white petal tips, white center eye and bright yellow in the mid-section.

'Wow312' can be most closely compared to *Delosperma cooperi* cultivars 'WOW2011-1' and 'Jewel of Desert Peridot'. 'WOW2011-1' and 'Jewel of Desert Peridot' are both similar to 'Wow312' in having yellow and white flowers. 'WOW2011-1' differs from 'Wow312' in having all yellow flower petals. 'Jewel of Desert Peridot' differs from 'Wow312' in having flower petals that are all yellow with large white centers.

BRIEF DESCRIPTION OF THE DRAWINGS

The accompanying colored photographs illustrate the overall appearance and distinct characteristics of the new *Delosperma*. The photographs were taken of a 2-liter container planted with 5 plants that were 3 months in age as grown in an unheated greenhouse in Noordwijkerhout, The Netherlands.

The photograph in FIG. 1 provides a side view of 'Wow312' in bloom.

Figure 1:
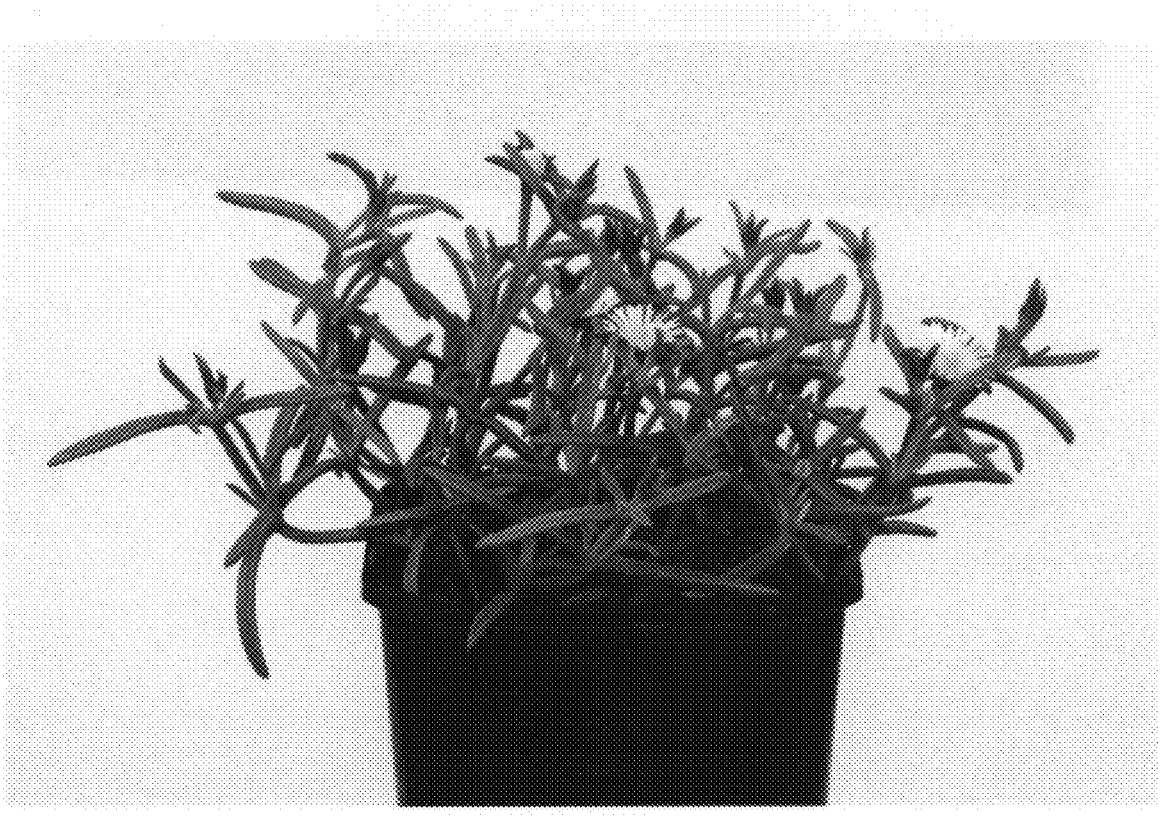
Figure 2:
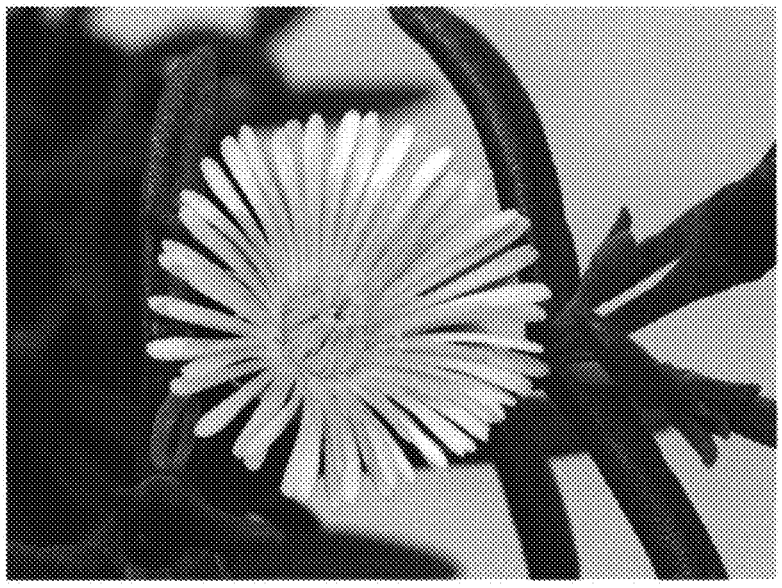

The photograph in FIG. 2 provides a close-up view of a flower of 'Wow312'.

Figure 3:
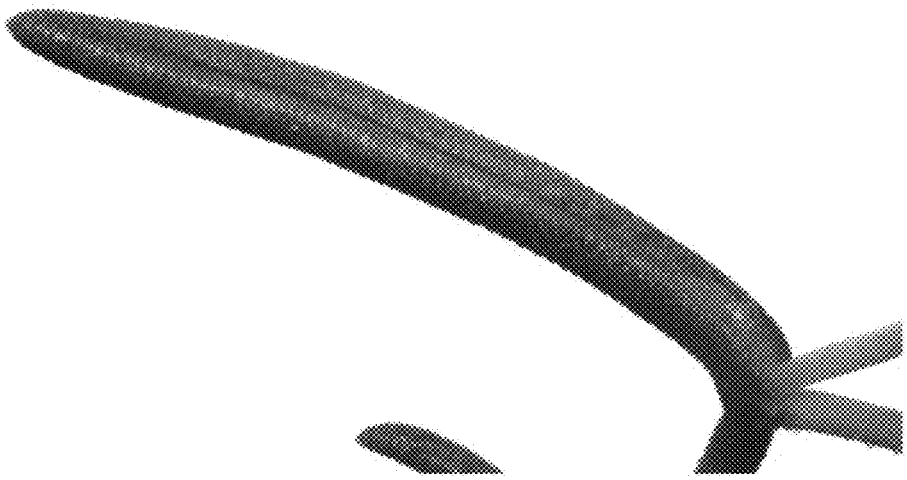

The photograph in FIG. 3 provides a close-up view of the foliage of 'Wow312'.

The colors in the photographs may differ slightly from the color values cited in the detailed botanical description, which accurately describe the colors of the new *Delosperma*.

DETAILED BOTANICAL DESCRIPTION

The following is a detailed description of 2-liter containers planted with 5 plants that were 3 months in age as grown in an unheated greenhouse in Noordwijkerhout, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Late spring to late summer in Noordwijkerhout, The Netherlands.

*Plant type*.—Herbaceous perennial.

*Plant habit*.—Compact, broad spreading and upright.

*Height and spread*.—Reaches about 15 cm in height and 17 cm in diameter.

*Cold hardiness*.—Observed to be hardy in U.S.D.A. Zones 7 to 12.

*Diseases and pests*.—No susceptibility to resistance to diseases or pests has been observed.

*Root description*.—Fibrous roots, 162D in color.

*Propagation*.—Softwood cuttings.

*Growth habit*.—Moderately to vigorous.

*Root development*.—Roots initiate and fill a 104-cell plug in 3 weeks and the planted plugs fully develop in 9-cm container within 6 weeks.

Stem description:

*Shape*.—Round.

*Stem color*.—Young stems; both surfaces 146D, mature stems; upper surface 176A, lower surface 148A to 148B.

*Stem size*.—Lateral branches; an average of 12.6 cm in length and 4 mm in diameter.

*Internode length*.—An average of 3.6 cm.

*Stem texture*.—Succulent.

*Stem surface*.—Slightly glossy, densely covered with very small glands, average length 0.2 mm, transparent and matching stem surface color.

*Stem aspect*.—Held at multiple angles, mainly upright.

*Stem strength*.—Strong.

*Branching habit*.—Freely branching, an average of 4 primary branches and 15 lateral branches per plant.

Foliage description:

*Leaf shape*.—Ligulate, triangular in cross-section, slightly carinate.

*Leaf substance*.—Succulent; an average of 4 mm in thickness.

*Leaf division*.—Simple.

*Leaf base*.—Cuneate.

*Leaf apex*.—Bluntly acute.

*Leaf venation*.—No veins visible.

*Leaf margins*.—Entire.

*Leaf aspect*.—Slightly curved.

*Leaf arrangement*.—Opposite.

*Leaf surface*.—Upper surface moderately glossy, lower surface slightly glossy, both surfaces smooth, densely covered with very small glands, average of 0.2 mm, transparent and matching stem surface color.

*Leaf color*.—Young upper and lower surface; 143C, mature upper surface; NN137B, lower surface; 138A.

*Leaf size*.—About 4.5 cm in length and 5 mm in width.

*Leaf quantity*.—Average of 8 (4 pairs) per lateral branch.

*Leaf attachment*.—Sessile.

Inflorescence description:

*Inflorescence type*.—Flowers solitary on terminus and axillary nodes.

*Flower number*.—An average of 4 flowers and 46 buds per plant.

*Flower fragrance*.—None.

*Flower aspect*.—Upright to slightly outward.

*Flower longevity*.—Average of 10 days, persistent.

*Flower type*.—Single, rotate.

*Flower size*.—Average of 2.9 cm in height and diameter, 1.2 cm in depth.

*Flower buds*.—Obovate in shape, an average of 1.4 cm in length and 9 mm in diameter, 146A to 146B in color, base 144B in color, surface is slightly glossy and densely covered with very short glandular hairs an average of 0.2 mm in length, transparent and matching bud surface color.

*Calyx*.—Rotate in shape, average of 8 mm in depth (including ovary) and 2 cm in diameter.

*Sepals*.—5, rotate, narrowly ovate in shape, margin entire, an average of 9 mm in length and 3.5 mm in width, bluntly acute apex, broadly cuneate base, color; when opening and fully open upper surface; NN137C, when opening and fully open lower surface; 147B, surface; upper and lower surface smooth and densely covered with very small glands average of 0.2 mm in length, transparent and matching surface color, upper surface glossy, lower surface moderately glossy.

*Petals*.—An average of 82 per flower, rotate, average of 2 whorls lower row an average of 46, upper row an average of 36, upper petal row; average of 8 mm in length, 2 mm in width, linear in shape, apex narrow acute, base narrowly cuneate, margin entire, glabrous and velvety surface, color; when opening upper and lower surface 4A to 4D, when fully open upper surface 4A, eye NN155D, when fully open lower surface 4C, lower petal row; average of 1.2 cm in length, 5 mm in width, narrow oblanceolate in shape, apex obtuse, base narrowly cuneate, margin entire, glabrous and velvety surface, color; when opening upper and lower surface a blend of 5D and NN155D, when fully open upper surface NN155D, changed to 5D at the base, when fully open lower surface NN155D, base 5D.

*Petaloids*.—None present.

*Peduncle*.—Average of 2.6 cm in length and 2 mm in diameter, held straight on top of lateral branch, 177A to 177B in color, surface is smooth, moderately glossy and densely covered with very small glands <0.2 mm in length, transparent and matching surface color.

*Pedicel*.—None present.

Reproductive organs:

*Pistils*.—5 occasionally 6, style; an average of 1 mm in length and 144A in color, stigma; deltoid in shape, an average of 2 mm in length and 1 mm in diameter, 12A in color, ovary; 147B, changing to 148A in color.

*Stamens*.—Average 100, anthers; oblong and basifixed in shape, an average of 0.75 mm in length and 0.4 mm in width, NN155D in color, filaments; 3.5 mm in length and a blend of NN155D and 4D in color, pollen; moderate in quantity and 9B in color.

*Fruit/seed*.—Fruit and seed production has not been observed to date.

It is claimed:

1. A new and distinct variety of *Delosperma* plant named 'Wow312' as described and illustrated herein.

* * * * *